United States Patent
Nakano

(10) Patent No.: US 10,076,885 B2
(45) Date of Patent: Sep. 18, 2018

(54) JOINING STATE DETERMINATION METHOD AND MOLDING DEVICE

(71) Applicant: BRIDGESTONE CORPORATION, Chuo-ku, Tokyo (JP)

(72) Inventor: Ryohei Nakano, Kodaira (JP)

(73) Assignee: BRIDGESTONE CORPORATION, Chuo-ku, Tokyo (JP)

( * ) Notice: Subject to any disclaimer, the term of this patent is extended or adjusted under 35 U.S.C. 154(b) by 0 days.

(21) Appl. No.: 15/121,117

(22) PCT Filed: Feb. 19, 2015

(86) PCT No.: PCT/JP2015/000789
§ 371 (c)(1),
(2) Date: Aug. 24, 2016

(87) PCT Pub. No.: WO2015/151392
PCT Pub. Date: Oct. 8, 2015

(65) Prior Publication Data
US 2017/0015075 A1    Jan. 19, 2017

(30) Foreign Application Priority Data

Apr. 2, 2014  (JP) ................................ 2014-075984

(51) Int. Cl.
*B32B 41/00*  (2006.01)
*B29D 30/30*  (2006.01)
(Continued)

(52) U.S. Cl.
CPC ..... *B29D 30/3007* (2013.01); *B29D 30/0061* (2013.01); *G01B 11/24* (2013.01);
(Continued)

(58) Field of Classification Search
CPC ........ B29D 30/0061; B29D 2030/0066; B29D 2030/3064; G01B 11/24; G01N 21/88; G01N 2201/062
(Continued)

(56) References Cited

U.S. PATENT DOCUMENTS 5,313,287 A  *  5/1994  Barton ................. H04N 1/4052
                                                       382/252
2012/0086950 A1    4/2012  Sho et al.
(Continued)

FOREIGN PATENT DOCUMENTS

| CN | 1985147 A | 6/2007 |
|---|---|---|
| CN | 103261836 A | 8/2013 |
| DE | 3926721 A1 | 2/1991 |
| DE | 102012016587 A1 | 2/2014 |
| EP | 1788346 A1 | 5/2007 |

(Continued)

OTHER PUBLICATIONS

May 2, 2018, Search Result of Office Action issued by the State Intellectual Property Office in the corresponding Chinese Patent Application No. 201580017822.3.

*Primary Examiner* — Michael N Orlando
*Assistant Examiner* — Joshel Rivera
(74) *Attorney, Agent, or Firm* — Kenja IP Law PC

(57) ABSTRACT

A joining state determination method includes: acquiring member front end imaging data of a band-shaped member; acquiring member joint imaging data of the band-shaped member; calculating a matching rate indicating a degree of coincidence of the acquired member joint imaging data with member front end registration data registered based on the acquired member front end imaging data; and determining that the longitudinal ends of the band-shaped member are properly joined, in the case where the calculated matching rate is either not greater than a predetermined threshold or less than the predetermined threshold.

5 Claims, 8 Drawing Sheets

(51) Int. Cl.
  G01B 11/24 (2006.01)
  G01N 21/88 (2006.01)
  B29D 30/00 (2006.01)
  G01M 17/02 (2006.01)
  G01N 21/952 (2006.01)
  G06T 7/00 (2017.01)
  G06T 7/50 (2017.01)

(52) U.S. Cl.
  CPC ............ *G01M 17/02* (2013.01); *G01N 21/88* (2013.01); *G01N 21/8851* (2013.01); *G01N 21/952* (2013.01); *G06T 7/0004* (2013.01); *G06T 7/50* (2017.01); *B29D 2030/0066* (2013.01); *B29D 2030/3064* (2013.01); *G01N 2201/062* (2013.01)

(58) Field of Classification Search
  USPC ................... 156/60, 64, 350, 351, 378, 379
  See application file for complete search history.

(56) References Cited

U.S. PATENT DOCUMENTS

| | | | | |
|---|---|---|---|---|
| 2012/0330447 | A1* | 12/2012 | Gerlach | ................ G01B 11/24 700/95 |
| 2013/0169974 | A1* | 7/2013 | Iwayama | ........... B29D 30/3007 356/601 |
| 2016/0236892 | A1 | 8/2016 | Kostka et al. | |

FOREIGN PATENT DOCUMENTS

| | | | |
|---|---|---|---|
| EP | 2735433 | A1 | 5/2014 |
| JP | H0587525 | A | 4/1993 |
| JP | 2007530962 | A | 11/2007 |
| JP | 2010101721 | A | 5/2010 |
| JP | 2011007633 | A | 1/2011 |
| JP | 2012220254 | A | 11/2012 |
| WO | 2006019070 | A1 | 2/2006 |
| WO | 2010020398 | A1 | 2/2010 |
| WO | 2013012082 | A1 | 1/2013 |

* cited by examiner

JOINING STATE DETERMINATION METHOD AND MOLDING DEVICE

TECHNICAL FIELD

The disclosure relates to a method of determining the joining state when winding a band-shaped member on a molding drum and joining both longitudinal ends of the band-shaped member to mold the band-shaped member into a cylindrical shape, and a molding device that performs the method.

BACKGROUND

For example when molding a member such as the tread of a tire, a band-shaped member is wound on a molding drum and both longitudinal ends of the band-shaped member are joined to mold the band-shaped member into a cylindrical shape. If the joining is defective, that is, if the longitudinal ends of the band-shaped member cannot be appropriately joined such as when a gap exists between the longitudinal ends, problems such as the thickness of the molded member being not uniform would ensue. In the case where such a joining defect occurs in, for example, the tread of a tire, there is a possibility that the dimensions of the manufactured tire are out of specifications or the tire has poor appearance due to degraded surface quality.

To detect such a joining defect, the positions of the starting end and terminating end of the band-shaped member need to be detected accurately. Patent Literature (PTL) 1 describes the technique of detecting the positions of the starting end and terminating end of the band-shaped member using a two-dimensional laser displacement sensor.

CITATION LIST

Patent Literature

PTL 1: WO 2006/019070 A1

SUMMARY

Technical Problem

However, in the case of detecting the positions of the starting end and terminating end of the band-shaped member by using a two-dimensional laser displacement sensor or the like, a blind spot from the sensor may exist in the joint of the longitudinal ends of the band-shaped member depending on the position of the sensor or the shape of the ends of the band-shaped member, which hinders the determination of the joining state such as a joining defect.

It could therefore be helpful to provide a joining state determination method that can, when winding a band-shaped member on a molding drum and joining both longitudinal ends of the band-shaped member to mold the band-shaped member into a cylindrical shape, reliably determine the joining state of the longitudinal ends of the band-shaped member, and a molding device capable of performing the method.

Solution to Problem

A joining state determination method according to the disclosure is a joining state determination method of, when winding a band-shaped member on a molding drum and joining both longitudinal ends of the band-shaped member to mold the band-shaped member into a cylindrical shape, determining a state of the joining, the joining state determination method including: a member front end imaging data acquisition step of acquiring member front end imaging data of one of the longitudinal ends of the band-shaped member that is first wound on the molding drum, after the winding of the band-shaped member on the molding drum starts and before the longitudinal ends of the band-shaped member are joined; a member joint imaging data acquisition step of acquiring member joint imaging data of the band-shaped member, after the longitudinal ends of the band-shaped member are joined; a first pattern matching step of calculating a matching rate indicating a degree of coincidence of the acquired member joint imaging data with member front end registration data registered based on the acquired member front end imaging data; and a first joining state determination step of determining that the longitudinal ends of the band-shaped member are properly joined, in the case where the matching rate calculated in the first pattern matching step is either not greater than a predetermined threshold or less than the predetermined threshold.

A molding device according to the disclosure is a molding device that performs the aforementioned joining state determination method, the molding device including: a molding drum on which a band-shaped member is wound; an imaging unit configured to acquire, by imaging, member front end imaging data and member joint imaging data of the band-shaped member; and a joining state determination unit configured to determine a state of joining of both longitudinal ends of the band-shaped member, wherein the joining state determination unit is configured to: acquire the member front end imaging data of one of the longitudinal ends of the band-shaped member that is first wound on the molding drum, after the winding of the band-shaped member on the molding drum starts and before the longitudinal ends of the band-shaped member are joined; acquire the member joint imaging data of the band-shaped member, after the longitudinal ends of the band-shaped member are joined; calculate a matching rate indicating a degree of coincidence of the acquired member joint imaging data with member front end registration data registered based on the acquired member front end imaging data; and determine that the longitudinal ends of the band-shaped member are properly joined, in the case where the matching rate calculated in the first pattern matching step is either not greater than a predetermined threshold or less than the predetermined threshold.

Advantageous Effect

It is thus possible to provide a joining state determination method that can reliably determine the joining state of the longitudinal ends of the band-shaped member, and a molding device capable of performing the method.

DETAILED DESCRIPTION

The following describes a molding device according to one of the disclosed embodiments with reference to drawings.

Figure 1:
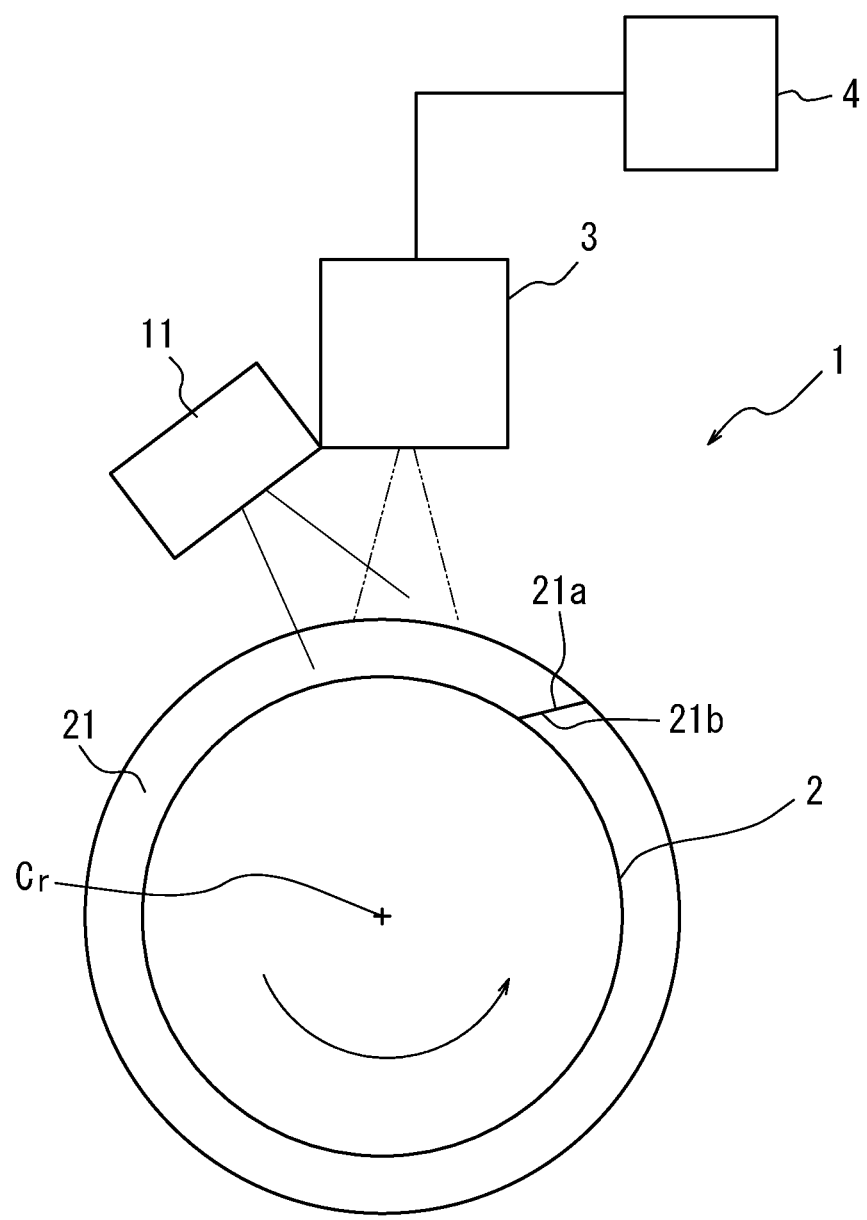
FIG. 1 is a side view illustrating a molding device according to one of the disclosed embodiments in a state where a band-shaped member is placed.

A molding device 1 according to one of the disclosed embodiments illustrated in FIG. 1 includes: a molding drum 2 on which a band-shaped member 21 such as the tread or belt of a tire is wound; an imaging unit 3 that acquires, by imaging, member front end imaging data which is an image of one of the longitudinal ends of the band-shaped member 21 first wound on the molding drum 2 when winding the band-shaped member 21 on the molding drum 2, and member joint imaging data which is an image of the joint and its vicinity when joining the longitudinal ends of the band-shaped member 21 after winding the band-shaped member 21 on the molding drum 2; and a joining state determination unit 4 that determines the joining state of the longitudinal ends of the band-shaped member.

The molding drum 2 is shaped like a column or a cylinder, and rotated about a central axis Cr by a drive unit such as a servomotor.

The imaging unit 3 captures images of at least the member front end (the longitudinal end 21 of the band-shaped member illustrated in FIGS. 4A to 4D) and member joint (the joint of the longitudinal ends 21a and 21b of the band-shaped member and its vicinity) of the band-shaped member 21 placed on the molding drum 2. The imaging unit 3 may be realized by an image sensor that converts the brightness of light emitted from an imaging object into an electrical signal, such as a CCD camera.

The imaging unit 3 is separated from the molding drum 2, and fixed to have its imaging direction toward the molding drum 2.

The joining state determination unit 4 in this embodiment stores member front end master data and joint crack shape registration data described later. The joining state determination unit 4 is connected to the imaging unit 3. The joining state determination unit 4 determines the joining state of the longitudinal ends of the band-shaped member, using the stored information and the member front end imaging data and member joint imaging data of the band-shaped member captured by the imaging unit 3. The joining state determination unit 4 may be realized by a computer system capable of executing program instructions such as a personal computer or other hardware. The connection between the joining state determination unit 4 and the imaging unit 3 may be wired or wireless.

The molding device 1 in this embodiment includes a control unit. The control unit controls the rotation of the molding drum 2, and gives the imaging unit 3 imaging instructions and the like. The control unit may be realized by a controller that controls operation according to a program such as a programmable logic controller (PLC).

The molding device 1 in this embodiment also includes a light source 11 including an LED or the like.

The light source 11 provides appropriate brightness for the imaging unit 3 to capture an image of the band-shaped member 21. The light source 11 allows the imaging unit 3 to capture an image without being affected by ambient brightness.

Figure 2A:
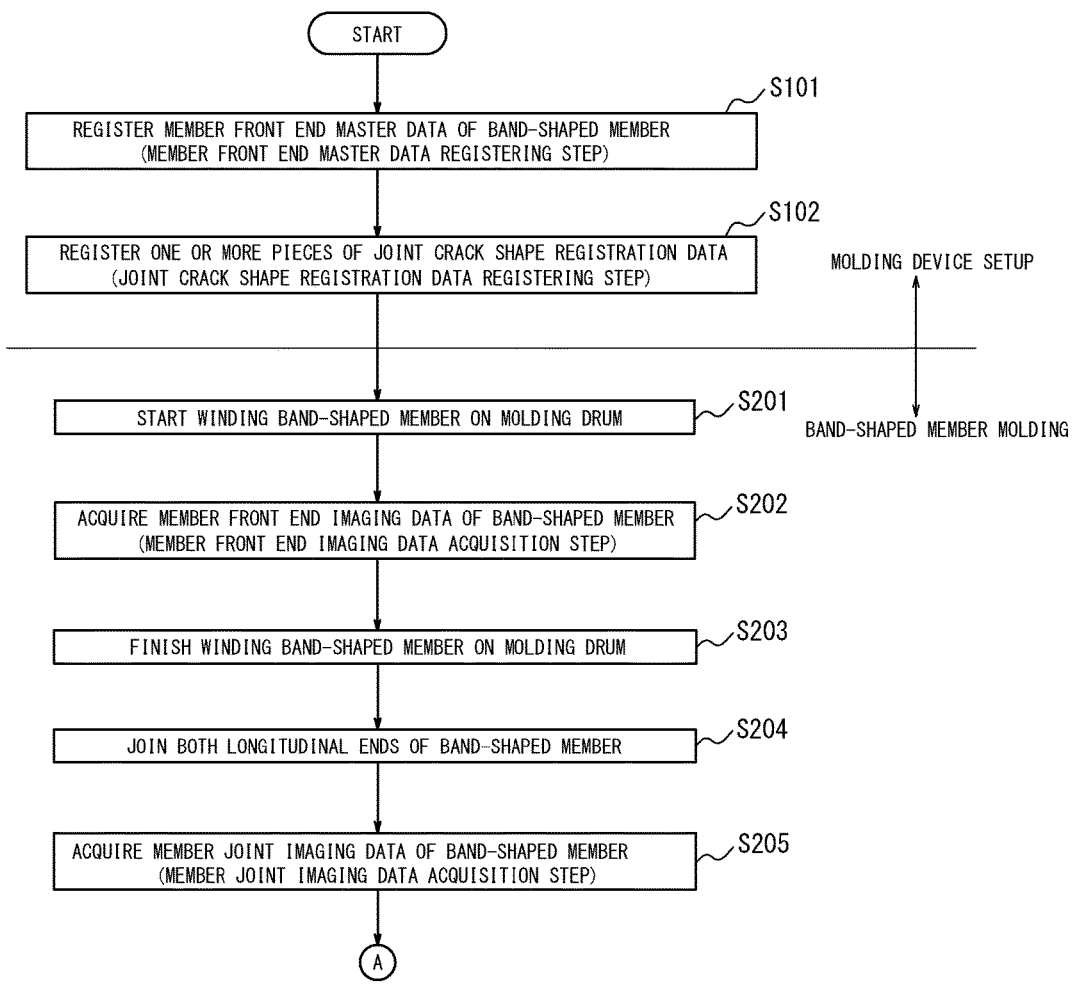
FIG. 2A is a flowchart of a joining state determination method according to one of the disclosed embodiments upon molding device setup and band-shaped member molding.
Figure 2B:
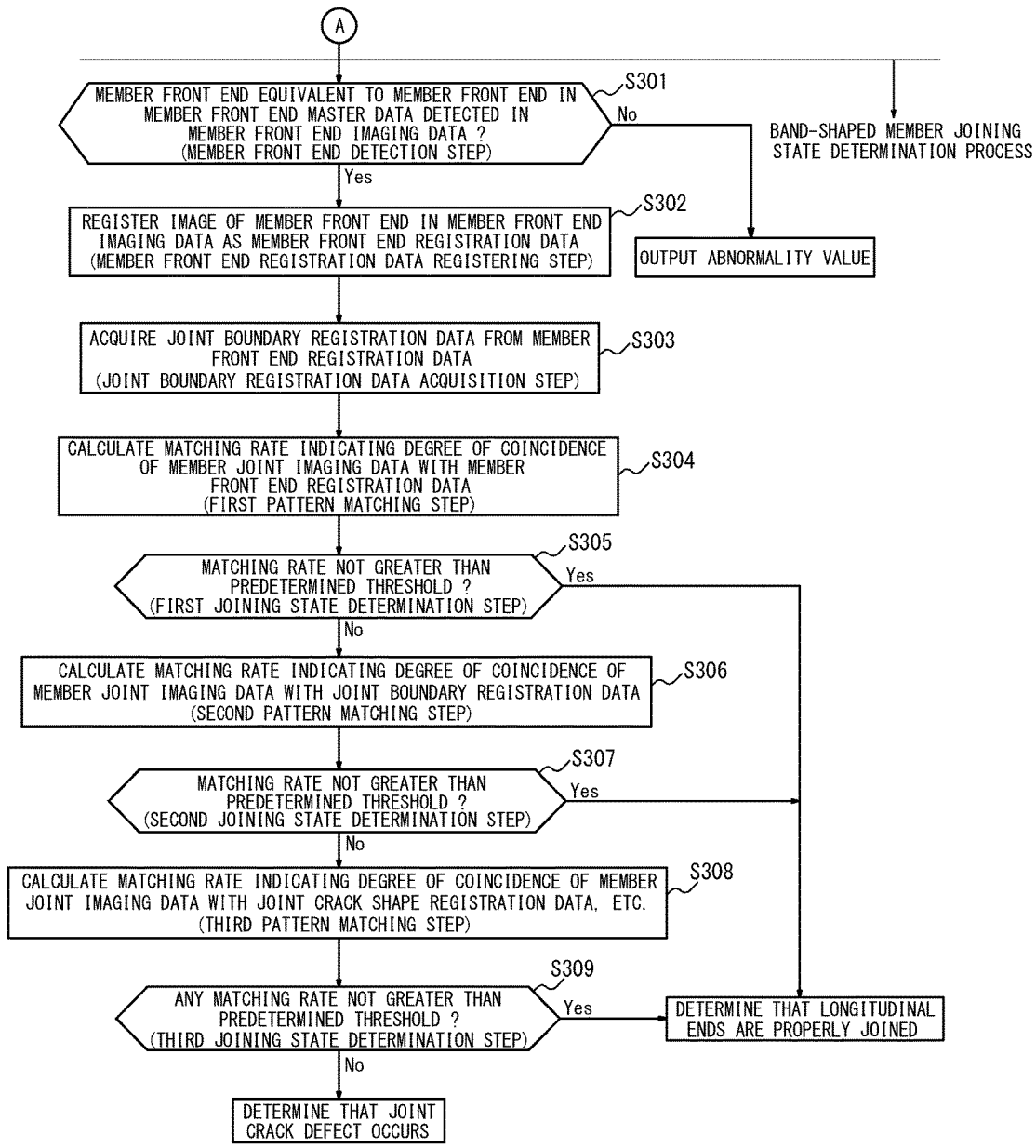
FIG. 2B is a flowchart of a band-shaped member joining state determination process in the joining state determination method according to one of the disclosed embodiments.

The following describes in detail a joining state determination method according to one of the disclosed embodiments by which the molding device 1 determines the joining state when winding the band-shaped member 21 on the molding drum 2 and joining the longitudinal ends of the band-shaped member 21, with reference to the flowcharts in FIGS. 2A and 2B.

Figure 3:
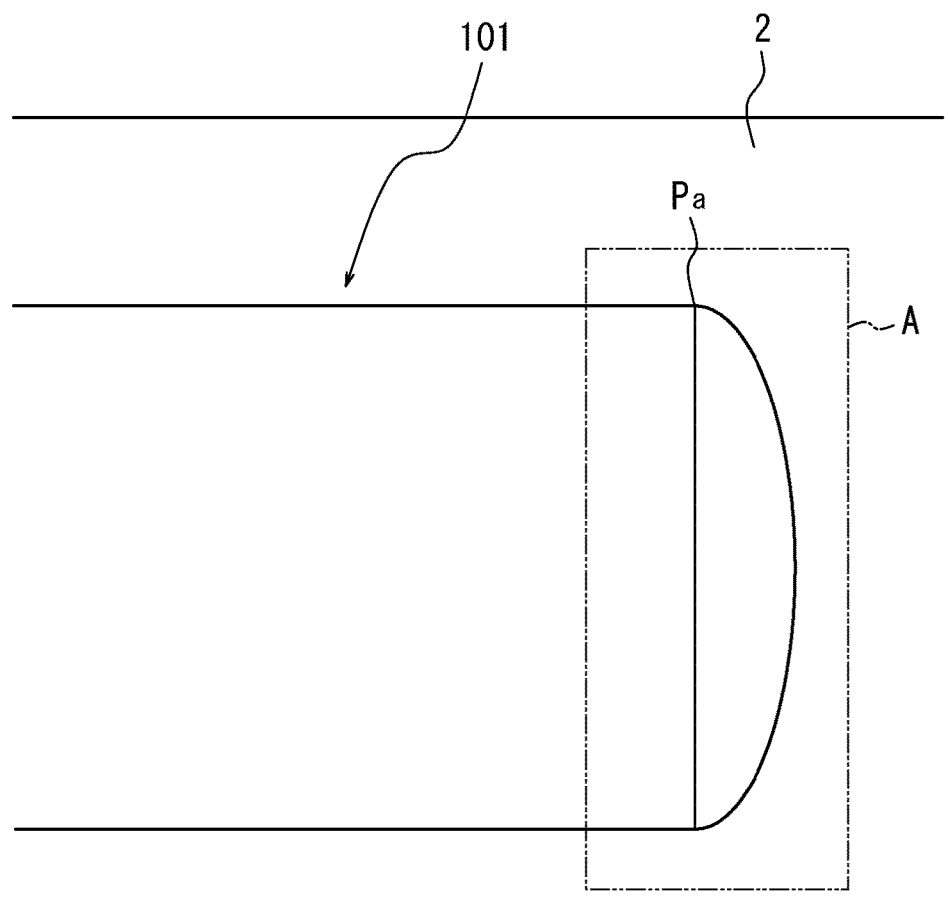
FIG. 3 is a diagram illustrating a member front end master image of a band-shaped member sample.

First, prior to the winding of the band-shaped member 21 on the molding drum 2, a member front end master data registering step is performed at least before a first pattern matching step described later (in this embodiment, before a member front end detection step described later) in this embodiment (step S101). In the member front end master data registering step, for example, member front end master data A of the band-shaped member including: a member front end master image of a band-shaped member sample; and position information of a member front end reference position Pa in the member front end master image illustrated in FIG. 3 is registered in advance. The band-shaped member sample is a member of the same type (for example, a tread in the case where the band-shaped member 21 is a tread) and the same size as the band-shaped member 21 and has been processed in the same way as the band-shaped member 21.

In this embodiment, for example, the member front end master data A is generated by placing a band-shaped member sample 101 on the molding drum 2 and capturing, by the imaging unit 3, an image of an area (the virtual area enclosed by the dashed-two dotted lines) including the member front end reference position Pa and member front end of the band-shaped member sample 101, as illustrated in FIG. 3. The member front end reference position Pa is one widthwise end of the cutting surface of the band-shaped member 21 in this embodiment. The member front end reference position Pa in the member front end master data A is then detected. The member front end master data A generated in this way is stored in the joining state determination unit 4.

A joint crack shape registration data registering step is performed for a third joining state determination step described later in this embodiment (step S102). In the joint crack shape registration data registering step, one or more pieces of joint crack shape registration data B which are each an image of at least one part of the joint of the band-shaped member in a state of having a joint crack defect are registered. The joint crack defect means the existence of a gap in at least one part between the longitudinal ends 21a and 21b of the band-shaped member. This step will be described in detail later.

Figure 4A:
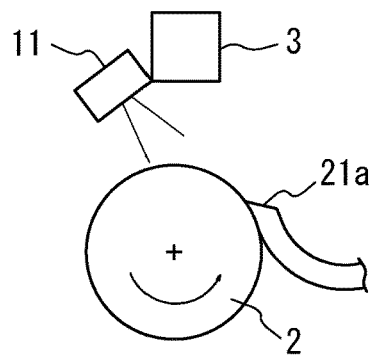
FIG. 4A is a side view illustrating each step when an imaging unit in the molding device acquires member front end imaging data and member joint imaging data of the band-shaped member.

One longitudinal end (member front end) 21a of the band-shaped member 21 to be molded is then placed on the molding drum 2 in the molding device 1 as illustrated in FIG. 4A, to start winding the band-shaped member 21 (step S201).

Figure 4B:
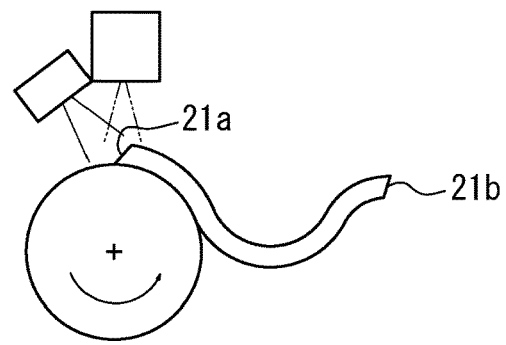
FIG. 4B is a side view illustrating each step when the imaging unit in the molding device acquires member front end imaging data and member joint imaging data of the band-shaped member.

After the winding of the band-shaped member 21 on the molding drum 2 starts, the longitudinal end 21a of the band-shaped member 21 moves in the circumferential direction of the molding drum 2 (counterclockwise in FIGS. 4A to 4D) with the rotation of the molding drum 2. A member front end imaging data acquisition step is performed when the longitudinal end 21a reaches the imaging position as illustrated in FIG. 4B in this embodiment, before joining the longitudinal ends of the band-shaped member 21 (step S202). In the member front end imaging data acquisition step, the imaging unit 3 acquires member front end imaging data C of the band-shaped member 21 by imaging. The imaging may be automatically performed by the control unit generating an imaging trigger when the longitudinal end 21a of the band-shaped member 21 reaches the imaging position.

Figure 4C:
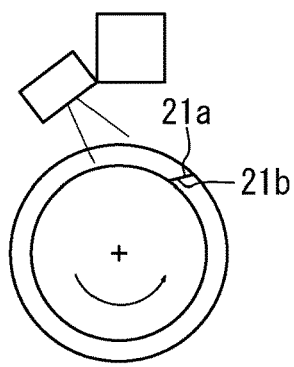
FIG. 4C is a side view illustrating each step when the imaging unit in the molding device acquires member front end imaging data and member joint imaging data of the band-shaped member.

Following this, the band-shaped member 21 is wound while rotating the molding drum 2. After finishing the winding (step S203), both longitudinal ends, i.e. the longitudinal ends 21a and 21b, of the band-shaped member 21 are joined as illustrated in FIG. 4C (step S204).

Figure 4D:
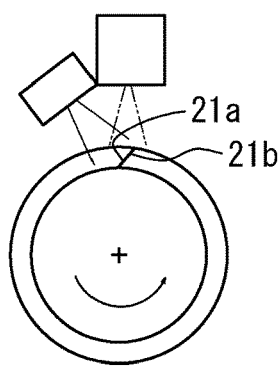
FIG. 4D is a side view illustrating each step when the imaging unit in the molding device acquires member front end imaging data and member joint imaging data of the band-shaped member.

After joining the longitudinal ends of the band-shaped member 21, the molding drum 2 is further rotated in this embodiment. When the joint of the band-shaped member 21 reaches the imaging position as illustrated in FIG. 4D, a member joint imaging data acquisition step is performed in this embodiment (step S205). In the member joint imaging data acquisition step, the imaging unit 3 acquires member joint imaging data D of the band-shaped member 21 by imaging. The imaging may be automatically performed in the same way as in step S202.

Following this, the joining state determination unit 4 in the molding device 1 determines the joining state of the longitudinal ends of the band-shaped member.

In the member front end detection step in this embodiment, whether or not a member front end equivalent to the member front end in the registered member front end master data A is detected in the acquired member front end imaging data C is determined (step S301). This member front end detection can be performed by subjecting the member front end imaging data C to pattern matching with the member front end master data A. In more detail, while relatively moving the member front end master data A and the member front end imaging data C, the two images are pattern matched. For example, the pattern matching may use a gray value correlation coefficient as a matching rate.

Such a member front end detection step can rule out any instance where the member front end imaging data C has not been appropriately acquired in the aforementioned member front end imaging data acquisition step.

In the case where a member front end equivalent to the member front end in the member front end master data A is not detected in the member front end imaging data C, e.g. in the case where the matching rate indicating the degree of coincidence of the acquired member front end imaging data C with the registered member front end master data A is either not greater than a predetermined threshold or less than the predetermined threshold in the pattern matching, an abnormality value is output to the control unit to end the process.

The member front end detection step may precede the member joint imaging data acquisition step (step S205), as long as it is after the member front end imaging data acquisition step (step S202). The threshold may be set as appropriate depending on the purpose.

In the case where a member front end equivalent to the member front end in the member front end master data A is detected in the acquired member front end imaging data C in the member front end detection step, e.g. in the case where the matching rate is either greater than the predetermined threshold or not less than the predetermined threshold in the pattern matching, the process advances to a member front end registration data registering step.

In the member front end registration data registering step, an image of the member front end in the member front end imaging data C is registered as member front end registration data C1 (step S302).

For example in the case where the appropriate acquisition of the member front end imaging data C is ensured sufficiently, the image of the member front end in the acquired member front end imaging data C may be registered as the member front end registration data C1 as it is without the member front end detection step, to perform the subsequent steps.

The band-shaped member 21 typically changes in shape depending on the ambient temperature and the like. In this embodiment, the joining state of the longitudinal ends of the band-shaped member is determined using the member front end registration data C1 based on the member front end imaging data C acquired during the molding and not the member front end master data A. Thus, the joining state can be stably determined without being affected by, for example, the change of the shape of the band-shaped member due to the change of the ambient temperature.

Figure 5:
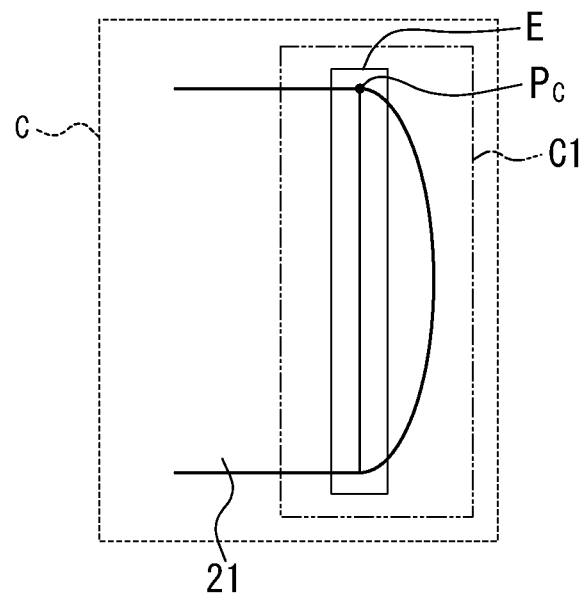
FIG. 5 is a diagram for describing a joint boundary registration data acquisition step.

Next, a joint boundary registration data acquisition step is performed in this embodiment (step S303). In the joint boundary registration data acquisition step, joint boundary registration data E which is an image of the member front end including a member front end reference position Pc is acquired from the member front end registration data C1, as illustrated in FIG. 5. The joint boundary registration data E is an image of a narrower area than the member front end registration data C1. For example, the joint boundary registration data E is generated by extracting a part that has, from the member front end reference position Pc of the member front end registration data C1, a predetermined width (e.g. the number of pixels equal to 1 mm) in each of the right and left directions (which substantially coincide with the longitudinal direction of the band-shaped member 21) of the image in the drawing.

In the first pattern matching step and first joining state determination step which follow in this embodiment, whether or not the member front end in the member joint imaging data D corresponding to the member front end registration data C1 is detected is determined. First, in the first pattern matching step, the acquired member joint imaging data D is subject to pattern matching with the member front end registration data C1 registered based on the acquired member front end imaging data C, to calculate a matching rate indicating the degree of coincidence of the member joint imaging data D with the member front end registration data C1 (step S304). The method of pattern matching is the same as that described with reference to the member front end detection step (step S301) except that the different images are used, and so its detailed description is omitted.

Figure 6A:
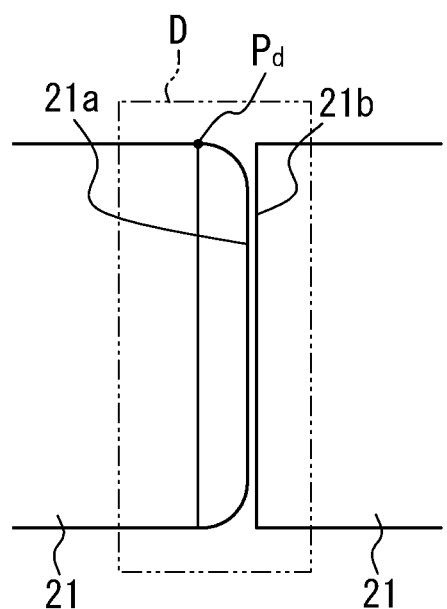
FIG. 6A is a diagram for describing a first pattern matching step, and illustrates a state where a gap exists between one longitudinal end and the other longitudinal end of the band-shaped member.

In the first joining state determination step, whether or not the matching rate calculated in the first pattern matching step is not greater than a predetermined threshold (50% in this embodiment) is determined (step S305). In the case where the matching rate is greater than the predetermined threshold, either the longitudinal ends of the band-shaped member are properly joined or a joining defect occurs. Accordingly, which of the cases applies is preferably determined in the subsequent steps. In the case where the matching rate is greater than the predetermined threshold, there is a possibility that a gap exists (a joint crack defect occurs) in at least one part between the longitudinal end 21a and the other longitudinal end 21b of the band-shaped member 21 as illustrated in FIG. 6A, or a misalignment (a joining state where the longitudinal end 21a and the other longitudinal end 21b of the band-shaped member 21 are out of alignment with each other in the width direction of the band-shaped member 21) occurs.

Figure 6B:
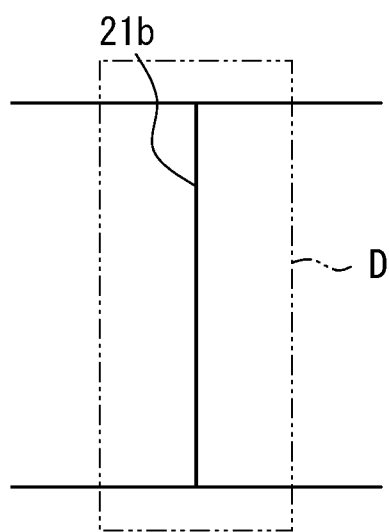
FIG. 6B is a diagram for describing the first pattern matching step, and illustrates a state where the longitudinal ends of the band-shaped member are properly joined.

In the case where the matching rate calculated in the first pattern matching step is not greater than the predetermined threshold, it can be determined that the longitudinal end 21a of the band-shaped member 21 is sufficiently wrapped (covered) with the other longitudinal end 21b of the band-shaped member 21 as illustrated in FIG. 6B. The joining state determination unit 4 accordingly can determine that the longitudinal ends of the band-shaped member 21 are properly joined, and end the process.

Although the criterion for determining that the longitudinal ends of the band-shaped member 21 are properly joined in step S305 is that the matching rate is "not greater than" the threshold in this embodiment, the criterion may be that the matching rate is "less than" the threshold. The same applies to the criteria in steps S307 and S309 described later. Whether the criterion is that the matching rate is "not greater than" the threshold or that the matching rate is "less than" the threshold is unequivocally (alternatively and exclusively) determined in design. For example, suppose the following control is defined: A maximum value of the matching rate with which the longitudinal ends of the band-shaped member 21 are determined as being properly joined is set, and whether or not the matching rate calculated in the first pattern matching step is "not greater than" the maximum value (threshold) is determined. In such a case, the control will never be subsequently changed to determine whether or not the matching rate is "less than" the threshold. Although the threshold is 50% as an example in this embodiment, the threshold may be set as appropriate depending on the purpose. The same applies to steps S307 and S309 described later.

By executing the aforementioned steps up to the first joining state determination step, the joining state of the longitudinal ends of the band-shaped member can be reliably determined.

Even in the case where the member front end is detected, i.e. the matching rate is greater than the predetermined threshold, in the first pattern matching step and the first joining state determination step, it does not necessarily mean that a joining defect such as a joint crack defect occurs, as the longitudinal ends of the band-shaped member may be properly joined.

Therefore, a second joining state determination step described later is preferably performed for more reliable determination of the joining state of the longitudinal ends of the band-shaped member.

After the first joining state determination step, a second pattern matching step is performed in this embodiment (step S306). In the second pattern matching step, the acquired member joint imaging data D is subject to pattern matching with the acquired joint boundary registration data E in a state where their member front end reference positions Pd and Pc coincide with each other, to calculate a matching rate indicating the degree of coincidence of the member joint imaging data D with the joint boundary registration data E. Since the joint boundary registration data E is an image of a narrower area than the member joint imaging data D, the matching rate mentioned here indicates the degree of coincidence of the area in the member joint imaging data D that is shown in the joint boundary registration data E with the joint boundary registration data E.

The second joining state determination step is then performed to determine whether or not the matching rate calculated in the second pattern matching step is not greater than a predetermined threshold (50% in this embodiment) (step S307).

In the case where the matching rate is greater than the predetermined threshold, either the longitudinal ends of the band-shaped member are properly joined or a joining defect such as a joint crack defect occurs. Accordingly, which of the cases applies is preferably determined in the subsequent steps.

In the case where the matching rate is not greater than the predetermined threshold, the joining state determination unit 4 may determine that the longitudinal ends of the band-shaped member 21 are properly joined, and may end the process.

Although the first joining state determination step and the second joining state determination step enable more reliable determination of the joining state of the band-shaped member, these steps alone may be still not sufficient for precisely determining whether or not a joining defect occurs. By further performing the third joining state determination step described later in the case of, for example, detecting a joint crack defect depending on the purpose, whether or not a joint crack defect occurs can be determined.

Figure 7:
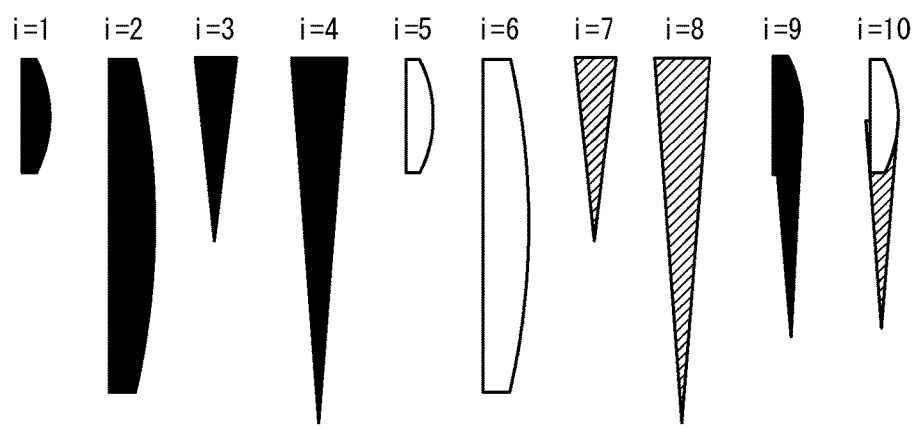
FIG. 7 is a diagram illustrating an example of joint crack shape registration data.

For the third joining state determination step, the joint crack shape registration data registering step is performed in advance in this embodiment, as mentioned earlier (step S102 in FIG. 2A). In this step, one or more images of at least one part of the joint of the band-shaped member in a state of having a joint crack defect as one kind of joining defects are registered in the joining state determination unit 4 in advance as the joint crack shape registration data B. For example, 10 types of patterns of shapes and colors illustrated in FIG. 7 are registered as joint crack shapes. In FIG. 7, the black color indicates the color of the upper surface of the band-shaped member 21, the white color indicates the color of the surface of the molding drum 2, and the oblique lines indicate the color of the cutting surface of the band-shaped member 21.

In a third pattern matching step in this embodiment, the acquired member joint imaging data D is subject to pattern matching with at least one of the registered joint crack shape registration data B and an image equivalent to it (hereafter collectively referred to as "joint crack shape registration data, etc."), to calculate a matching rate indicating the degree of coincidence of the member joint imaging data D with the joint crack shape registration data, etc. (step S308).

In the third joining state determination step, whether or not any of the at least one matching rate calculated in the third pattern matching step, i.e. the matching rate of the member joint imaging data D and any of the joint crack shape registration data, etc., is not greater than a predetermined threshold is determined (step S309). In the case where any matching rate is greater than the predetermined threshold, the joining state determination unit 4 determines that a joint crack defect occurs, and ends the process. In the case where each matching rate is not greater than the predetermined threshold, it is determined that the longitudinal ends of the band-shaped member 21 are properly joined, the process is finished.

If a large number of pieces of joint crack shape registration data are generated, the accuracy of joint crack defect determination can be improved. This, however, requires high cost to generate such joint crack shape registration data. Hence, one or more new images may be generated by scaling joint crack shape registration data in the longitudinal direction and/or width direction of the band-shaped member in the range of 0.5 times to 1.5 times as an example and/or rotating an image in the joint crack shape registration data in the range of −10° to +10° as an example, thus obtaining images equivalent to an image of the joint crack. Then, the matching rate indicating the degree of coincidence of the member joint imaging data with at least one of the image of the joint crack and the new images equivalent to the image of the joint crack is calculated in the third pattern matching step.

With this method, a large number of images can be generated by combining a plurality of pieces of joint crack shape registration data and a plurality of scaling factors and/or a plurality of rotation angles. Through pattern matching on at least one of these images and the member joint imaging data D, various types of joint crack defects may be determined even when the number of pieces of joint crack shape registration data is limited. This improves determination performance, and ensures robustness. The joining state of the longitudinal ends of the band-shaped member may thus be determined with high accuracy.

REFERENCE SIGNS LIST 1 molding device
2 molding drum
3 imaging unit
4 joining state determination unit
11 light source
21 band-shaped member
101 band-shaped member sample

The invention claimed is:

1. A joining state determination method of, when winding a band-shaped member on a molding drum and joining both longitudinal ends of the band-shaped member to mold the band-shaped member into a cylindrical shape, determining a state of the joining, the joining state determination method comprising:
a member front end imaging data acquisition step of acquiring member front end imaging data of one of the longitudinal ends of the band-shaped member that is first wound on the molding drum, after the winding of the band-shaped member on the molding drum starts and before the longitudinal ends of the band-shaped member are joined;
a member joint imaging data acquisition step of acquiring member joint imaging data of the band-shaped member, after the longitudinal ends of the band-shaped member are joined;
a first pattern matching step of using a gray value coefficient to calculate a matching rate indicating a degree of coincidence of the acquired member joint imaging data with member front end registration data registered based on the acquired member front end imaging data;
a first joining state determination step of determining that the longitudinal ends of the band-shaped member are properly joined, in the case where the matching rate calculated in the first pattern matching step is either not greater than a predetermined threshold or less than the predetermined threshold;
a joint boundary registration data acquisition step of acquiring joint boundary registration data which is an image of a member front end including a member front end reference position, from the member front end registration data;
a second pattern matching step of calculating a matching rate indicating a degree of coincidence of the acquired member joint imaging data with the acquired joint boundary registration data, in the case where the matching rate is either greater than the predetermined threshold or not less than the predetermined threshold in the first joining state determination step;
a second joining state determination step of determining that the longitudinal ends of the band-shaped member are properly joined, in the case where the matching rate calculated in the second pattern matching step is either not greater than a predetermined threshold or less than the predetermined threshold;
a joint crack shape registration data registering step of registering in advance one or more pieces of joint crack shape registration data which are each an image of at least one part of a joint of the band-shaped member in a state of having a joint crack defect as the state of the joining and which include patterns of shapes and colors of the joint crack defect, the joint crack defect being existence of a gap in at least one part between the longitudinal ends of the band-shaped member;
an equivalent image generating step of scaling the joint crack shape registration data in the longitudinal direction and/or width direction of the band-shaped member in the range of 0.5 times to 1.5 times and/or rotating the image in the joint crack shape registration data in the range of −10° to +10° to obtain an image equivalent to an image of the joint crack shape registration data;
a third pattern matching step of calculating a matching rate indicating a degree of coincidence of the acquired member joint imaging data with at least one of the registered joint crack shape registration data and the image equivalent to the joint crack shape registration data, in the case where the matching rate is either greater than the predetermined threshold or not less than the predetermined threshold in the second joining state determination step; and
a third joining state determination step of determining that the longitudinal ends of the band-shaped member are properly joined, in the case where the matching rate calculated in the third pattern matching step is either not greater than a predetermined threshold or less than the predetermined threshold.

2. The joining state determination method according to claim 1, further comprising
a member front end master data registering step of registering member front end master data of the band-shaped member in advance before the first pattern matching step, the member front end master data including a member front end master image of a band-shaped member sample,
wherein in the case where a member front end equivalent to a member front end in the registered member front end master data is detected in the acquired member front end imaging data, an image of the member front end is registered as the member front end registration data.

3. A molding device that winds a band-shaped member on a molding drum and joins both longitudinal ends of the band-shaped member to mold the band-shaped member into a cylindrical shape, the molding device comprising:

the molding drum on which the band-shaped member is wound;

an imaging unit configured to acquire, by imaging, member front end imaging data of one of the longitudinal ends of the band-shaped member that is first wound on the molding drum, and member joint imaging data; and a joining state determination unit configured to determine a state of the joining of the longitudinal ends of the band-shaped member, wherein the joining state determination unit is configured to:

acquire the member front end imaging data of one of the longitudinal ends of the band-shaped member that is first wound on the molding drum, after the winding of the band-shaped member on the molding drum starts and before the longitudinal ends of the band-shaped member are joined;

acquire the member joint imaging data of the band-shaped member, after the longitudinal ends of the band-shaped member are joined;

use a gray value coefficient to calculate a first matching rate indicating a degree of coincidence of the acquired member joint imaging data with member front end registration data registered based on the acquired member front end imaging data;

determine that the longitudinal ends of the band-shaped member are properly joined, in the case where the calculated first matching rate is either not greater than a predetermined first threshold or less than the predetermined first threshold;

acquire joint boundary registration data which is an image of a member front end including a member front end reference position, from the member front end registration data;

calculate a second matching rate indicating a degree of coincidence of the acquired member joint imaging data with the acquired joint boundary registration data, in the case where the second matching rate is either greater than the predetermined first threshold or not less than the predetermined first threshold;

a second joining state determination step of determining that the longitudinal ends of the band-shaped member are properly joined, in the case where the calculated second matching rate is either not greater than a second predetermined threshold or less than the predetermined second threshold;

register in advance one or more pieces of joint crack shape registration data which are each an image of at least one part of a joint of the band-shaped member in a state of having a joint crack defect as the state of the joining and which include patterns of shapes and colors of the joint crack defect, the joint crack defect being existence of a gap in at least one part between the longitudinal ends of the band-shaped member;

scaling the joint crack shape registration data in the longitudinal direction and/or width direction of the band-shaped member in the range of 0.5 times to 1.5 times and/or rotating the image in the joint crack shape registration data in the range of −10° to +10° to obtain an image equivalent to an image of the joint crack shape registration data;

calculate a third matching rate indicating a degree of coincidence of the acquired member joint imaging data with at least one of the registered joint crack shape registration data and the image equivalent to the joint crack shape registration data, in the case where the third matching rate is either greater than the predetermined second threshold or not less than the predetermined second threshold; and determine that the longitudinal ends of the band-shaped member are properly joined, in the case where the calculated third matching rate is either not greater than a predetermined third threshold or less than the predetermined third threshold.

4. The joining state determination method according to claim 2, wherein while relatively moving the member front end master data and the member front end imaging data, the member front end master image and the image of the member front end are pattern matched.

5. The joining state determination method according to claim 1, wherein the matching rate calculated in the second patter matching step indicates the degree of coincidence of the area in the acquired member joint imaging data that is shown in the joint boundary registration data with the acquired joint boundary registration data.

* * * * *